US008647578B2

(12) United States Patent
Melpignano

(10) Patent No.: US 8,647,578 B2
(45) Date of Patent: Feb. 11, 2014

(54) DEVICE TO DETECT ANALYTES IN A BIOLOGICAL SAMPLE

(75) Inventor: Patrizia Melpignano, Moruzzo (IT)

(73) Assignee: OR-EL Organska Elektronika D.O.O., Kobarid (SI)

( * ) Notice: Subject to any disclaimer, the term of this patent is extended or adjusted under 35 U.S.C. 154(b) by 7 days.

(21) Appl. No.: 13/503,275

(22) PCT Filed: Oct. 20, 2010

(86) PCT No.: PCT/IB2010/002682
§ 371 (c)(1), (2), (4) Date: Apr. 20, 2012

(87) PCT Pub. No.: WO2011/048472
PCT Pub. Date: Apr. 28, 2011

(65) Prior Publication Data
US 2012/0213670 A1 Aug. 23, 2012

(30) Foreign Application Priority Data

Oct. 21, 2009 (IT) .............................. UD2009A0187

(51) Int. Cl.
*G01N 21/00* (2006.01)
(52) U.S. Cl.
USPC .................. 422/82.05; 422/82.07; 422/82.08; 422/426; 422/430; 436/63; 436/172; 436/518; 436/536
(58) Field of Classification Search
USPC ................ 422/82.05, 82.07, 82.08, 426, 430; 436/63, 172, 518, 536
See application file for complete search history.

(56) References Cited

U.S. PATENT DOCUMENTS

| 2002/0095073 | A1 | 7/2002 | Jacobs et al. |
| 2005/0191694 | A1 | 9/2005 | Jacobs et al. |
| 2007/0210322 | A1 | 9/2007 | Ohsawa et al. |
| 2007/0285010 | A1 * | 12/2007 | Lee et al. ...................... 313/504 |
| 2008/0277606 | A1 | 11/2008 | Wang et al. |
| 2010/0173797 | A1 | 7/2010 | Jacobs et al. |
| 2010/0320446 | A1 | 12/2010 | Kang et al. |

FOREIGN PATENT DOCUMENTS

| WO | 2007 054710 | 5/2007 |
| WO | 2008 097046 | 8/2008 |

OTHER PUBLICATIONS

International Search Report Issued Jan. 11, 2011 in PCT/IB10/02682 Filed Oct. 20, 2010.

* cited by examiner

*Primary Examiner* — Lyle Alexander
(74) *Attorney, Agent, or Firm* — Oblon, Spivak, McClelland, Maier & Neustadt, L.L.P.

(57) ABSTRACT

Device to detect at least an analyte, comprising a transparent substrate (2), having a first surface (3) with which a light source (7) is associated, and a second surface (4) on which a plurality of biological protein probes (12) are disposed, a layer (6) of polymer being interposed between said second surface (4) and said biological protein probes (12). A marker (fluorophore) is associated with said analyte, having determinate characteristics of fluorescence and/or phosphorescence correlated to the emission wavelength of the light source (7). Said light source (7) is suitable to emit a light radiation in a range of wavelengths equal to 400-550 nm, inside which range the absorption peak of said marker (fluorophore) used is comprised. The value of the distance ("s") between the wavelength corresponding to the absorption peak of the marker (fluorophore) and the wavelength corresponding to the emission peak of fluorescence (phosphorescence) is comprised between 25 and 150 nm.

33 Claims, 2 Drawing Sheets

DEVICE TO DETECT ANALYTES IN A BIOLOGICAL SAMPLE

FIELD OF THE INVENTION

The present invention concerns a device to detect at least an analyte in a biological sample. In particular, the device according to the present invention consists of a miniaturized device comprising, in a single structure, a thin, flat light source (for example, but not exclusively, of the OLED type) able to emit a radiation with an emission spectrum optimized for exciting a marker, for example a fluorophore, linked to one or more biological probes.

The device according to the invention is intended preferentially for the diagnostics of protein molecules (antibodies-antigens) inside a sample (immune-diagnostics), but also for ultra-fast bio-molecular diagnostics to detect molecules of nucleic acid, or to detect structures marked with fluorophores in cell structures.

BACKGROUND OF THE INVENTION

Miniaturized devices to detect analytes in biological samples are known, comprising a light source and a system containing the sample.

For example, the international patent application WO-A-2005/103652 describes a miniaturized device that comprises a light source consisting of an OLED (Organic Light Emitting Diode) system, diffraction filters to direct the light emitted by the light source toward the sample to be analyzed, and other diffraction layers suitable to direct the light emitted by the sample to the detection system. The device described in the application WO-A-2005/103652 provides that the wavelengths of the light emitted by the light source are selected so as to transmit to the sample only the wavelengths concerned in stressing the sample, where said selection is made through the creation of vertical cavities inside the OLED layer.

Another state-of-the art device is described in the international patent application WO-A-2007/097572 which provides not only a light source consisting of a LED (Light Emitting Diode) system but also a layer of material intended to form a stable link with the sample to be analyzed directly applied on the light source. The layer essentially consists of a surface functionalized by means of suitable linker molecules able to fix the analyte molecules stably. The wavelengths of the light emitted by the light source are controlled using a system known as quantum dot.

Another miniaturized device for detecting an analyte in a biological sample is described in the international patent application WO-A-03/060461, which describes in general terms a device comprising a light source, a first system of filters for transmitting the light to the sample and a detector system able to detect the light emitted by the sample, where the light emitted by the sample is directed to the detector system through a second system of filters.

Moreover, the international patent application WO-A-2007/054710 describes a device comprising an OLED source for the emission of light necessary to excite the sample contained in a microfluid system and a detector system located in direct contact with the microfluid system. The device described therein provides that the micro-channels that make up the microfluid system consist of polydimethylsiloxane doped with suitable coloring agents, the function of which is to absorb the wavelengths of light emitted by the OLED source which could interfere with the analysis of the sample and are therefore able to transmit to the sample only the light wavelengths useful to carry out the analysis.

The US patent application US-A-2003/035755 describes a device that has an OLED-type light source on which a microfluid device is positioned, able to contain the sample to be analyzed, and also comprises, in succession, a layer of lenses to focus the light emitted by the sample, a layer defined as pinhole layer and another filter followed by the detector system. The layer of lenses, the pinhole layer and the other filter are components suitable to focus and filter the light emitted by the sample to be analyzed so as to eliminate the wavelengths that could interfere with the analysis.

The international patent application WO-A-2007/107947 describes a micro-electronic device to detect an analyte in a sample, characterized by the presence of heating electrodes and field electrodes. The function of the latter is to induce the movement/flow of the sample inside the device. The heating electrodes are intended to heat the sample and can be coupled with Peltier cells in order to effect thermal cycles of heating and cooling so as to conduct the relative analysis.

The US patent application US 2002/095073, which defines the closest state of the art to the present invention, describes a wide range of bio-chips in which the biological probes are disposed on a transparent substrate, such as glass or plastic, and in which the latter can possibly be inserted in a microfluid circuit for the circulation of the biological fluid examined.

This document describes the possible use of an OLED or LED source under the micro-array of probes deposited on the same slide. The document has problems concerning the sensitivity of detection inasmuch as, since the intensity of an OLED or LED source can be from 100,000 to 1,000 times higher than the intensity emitted by a possible marker, such as for example a fluorophore, this makes it impossible to detect the latter without the appropriate use of particular optical devices, which are not described in U.S. Pat. No. '073.

Although miniaturized devices to detect an analyte in a biological sample have already been described and marketed, there is a continuing need to develop devices that allow to conduct analyses that are increasingly sensitive and specific by operators who are not specialized, that is, not belonging to analysis laboratories, but by medics at the so-called "points of care", where the analysis must be carried out in real time, in the presence of the patient.

Purpose of the present invention is to provide an improved device that allows to conduct analyses of this type with optimized reaction conditions in order to increase the sensitivity and specificity of the analysis, and also to reduce the times needed to carry out the analysis. In particular, the purpose of the present invention is to perfect a miniaturized device that allows a simultaneous analysis relating to the presence of several pathogens in the biological sample analyzed.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

In accordance with the above purpose, a device to detect at least an analyte in a biological sample according to the present invention comprises a transparent substrate, made of glass or plastic material or similar, having a first surface or surface which is lower during use, to which a light source is applied, preferably but not exclusively consisting of an OLED system The transparent substrate comprises a second surface, or surface which is upper during use, able to support a plurality of biological protein probes, disposed in a desired geometry, to form for example a matrix or array connected to the second surface of the substrate by means of a polymer. The polymer guarantees that the probes adhere on the upper surface of the substrate thanks to the activation of a covalent link with the proteins that make up the protein probes. The polymer can be distributed on the surface either by means of immersion or dipping, or by means of another depositing procedure, which is irrelevant for the purposes of the invention. The plurality of probes will then be contained inside a microfluid system made of transparent plastic material, for example PMMA polymethyl methacrylate, and obtained for example by injection molding.

The microfluid system is attached to the transparent substrate, which has the light source on its lower side, in a known manner, for example by means of a system with clips, and the hydraulic seal is achieved by means of an O-ring.

The analyte to be detected may preferably consist of protein molecules, for example antigens or antibodies, or molecules of nucleic acids, for example genes or parts of genes.

A marker element is linked to the analyte to be detected and consists, in the preferential solution of the invention, of a fluorophore, having determinate characteristics of fluorescence or phosphorescence emission, suitably coordinated to the wavelength of the incident light radiation.

In a preferred solution of the invention, in order to maximize the detection sensitivity of the signal emitted by the fluorophore, a filter or advantageously two filters are used.

The first filter, made on the glass or plastic support, can be used directly as a growth substrate of the OLED device, or positioned directly on the face the radiation exits from.

In a preferred solution of the invention, the filter has a transmittance lower than $2.0*10-6$ outside the wavelength, for example comprised between 400 and 550 nm, corresponding to the emission peak of the fluorophore, and a transmittance $>0.6$ to the peak wavelength of the source emission spectrum.

The sample to be analyzed will be deposited directly on the face the radiation exits from, possibly contained in a microfluid system.

In a preferred solution of the invention, the second filter, of the band-pass type, has a transmittance $>0.8$ in correspondence with the emission peak of the fluorophore with FWHM comprised between 20 and 40 nm and a transmittance $>0.01$ outside this range.

In this way, by focusing the light source emission spectrum, thanks to the filtering system, in correspondence with the absorption peak of the marker, and by cutting sharply the emissions at frequencies above that corresponding to the absorption peak, the device according to the invention allows to maximize the detection sensitivity in that the emission of the markers (fluorophores) is optimized and is not invalidated by the relatively high light intensity emitted by the OLED source.

BRIEF DESCRIPTION OF THE DRAWINGS

These and other characteristics of the present invention will become apparent from the following description of a preferential form of embodiment, given as a non-restrictive example with reference to the attached drawings wherein.

Figure 1:
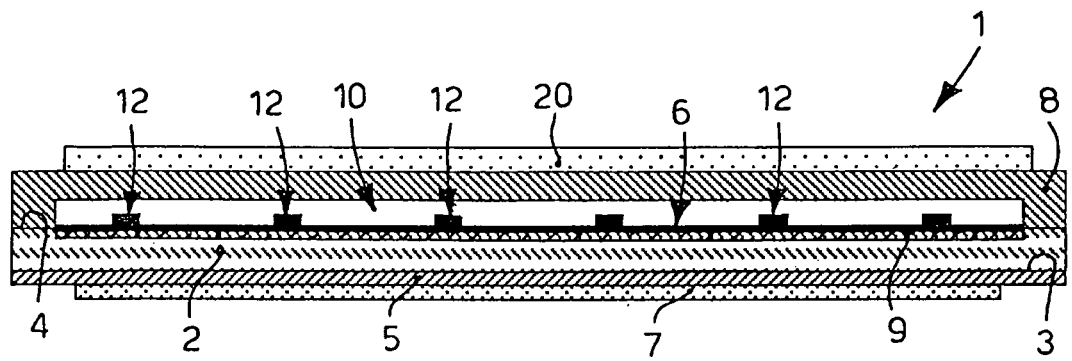
FIG. 1 is a schematic vertical section of a device to detect analytes in a biological sample according to the present invention.
Figure 2:
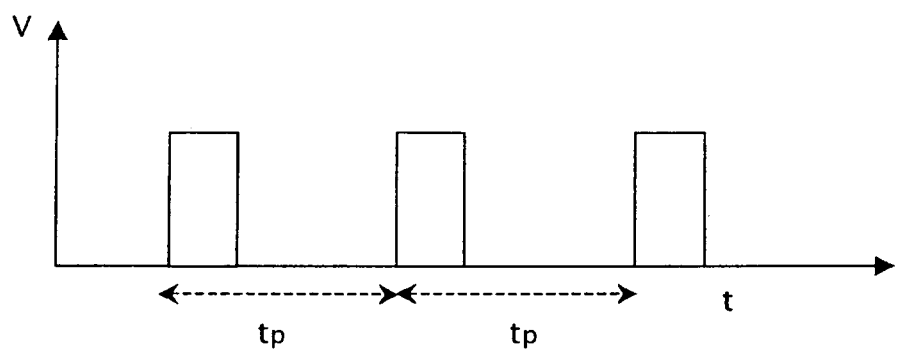
FIG. 2 is a first temporal diagram of the electric feed of the device in FIG. 1.
Figure 3:
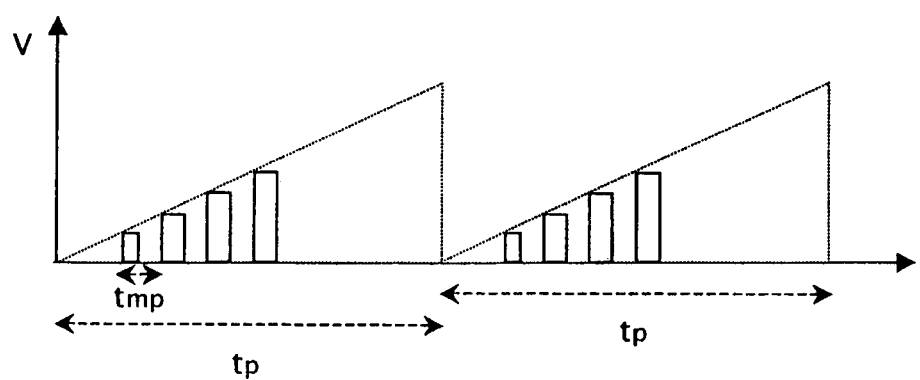
FIG. 3 is a second temporal diagram of the electric feed of the device in FIG. 1.

To facilitate comprehension, the same reference numbers have been used, where possible, to identify common elements in the drawings that are substantially identical. It is understood that elements and characteristics of one form of embodiment can conveniently be incorporated into other forms of embodiment without further clarifications.

DETAILED DESCRIPTION OF A PREFERENTIAL FORM OF EMBODIMENT

With reference to FIG. 1, in a preferred form of embodiment, a device 1 to detect analytes in a biological sample, hereafter for brevity called biochip, comprises a transparent substrate 2 having a first surface 3, or surface which is lower during use, on which a thin film of transparent conductive material is applied, not shown in the drawings. The biochip 1 also comprises an optical source 7 in direct contact with the film of transparent conductive material and a microfluid circuit or system 8, suitable to contain the sample to be analyzed and the markers, for example fluorophores, to detect the relative analyte in direct contact with a second, upper surface 4 of the transparent substrate 2.

On the opposite side of the optical source a detector device 20 is disposed, described in more detail hereafter.

The optical source 7, in a preferred form of embodiment of the biochip 1 according to the present invention, is made using thin organic film technology on a transparent substrate, also known as OLED (Organic Light Emitting Diode). The source is able to emit a light radiation with a fixed emission peak, but selectable from any wavelength whatsoever in order to induce emissions of radiations in a suitable fluorescent or phosphorescent marker (fluorophore) used to specifically detect the desired analyte.

Figure 4:
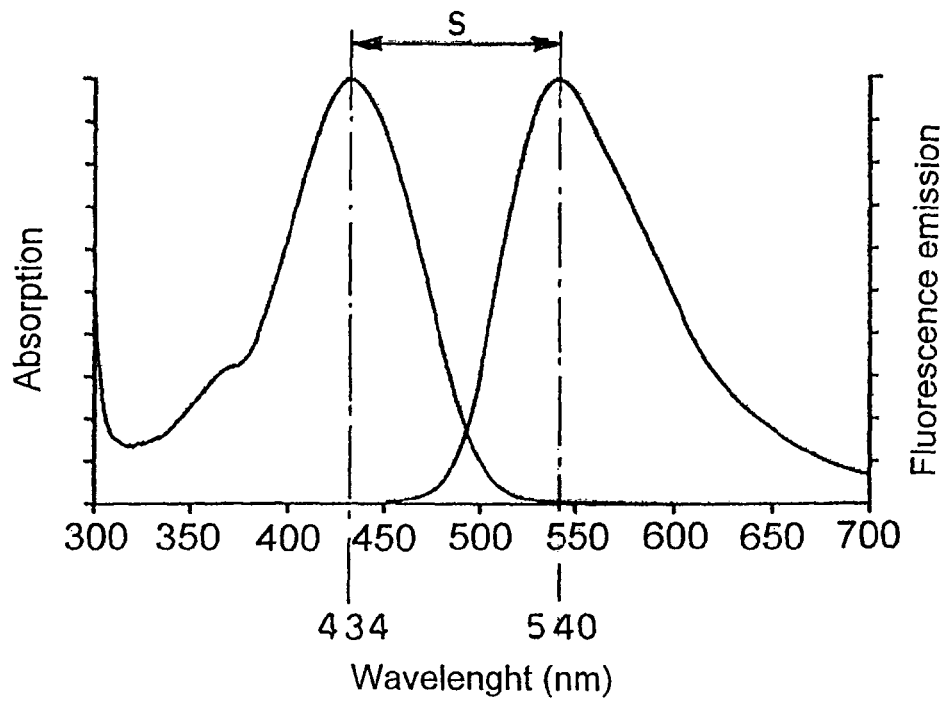
FIG. 4 shows the absorption and emission spectrums of the marker (fluorophore) used in the device according to the present invention and associated with the OLED source.

FIG. 4, discussed in more detail hereafter, shows an emission spectrum referred to the development of the absorption of the fluorophore (absorption peak in this case at about 434 nm) and the characteristics of fluorescent emission by the fluorophore (maximum fluorescence emission at 540 nm).

The analyte-may consist of:

i) a molecule of nucleic acid: in this case the marker consists of a probe of nucleic acids linked to a fluorescent or phosphorescent molecule (fluorophore) able to emit a fluorescent or phosphorescent radiation;

ii) a protein molecule; in this case the marker consists for example of a specific antibody for the molecule linked to a fluorescent or phosphorescent molecule able to emit a fluorescent or phosphorescent radiation;

iii) a cell culture selectively marked with a fluorescent or phosphorescent molecule able to emit a fluorescent or phosphorescent radiation.

The optical source 7 is able to emit a peak wavelength such as to correspond to the maximum absorption spectrum of the markers.

According to the invention, the wavelength is comprised between 400 and 550 nm, so as to comprise the absorption peak also as the type of fluorophore used as marker varies. The emission intensity of the source must be such as to allow the marker to be excited and therefore must be particularly high. In order to achieve this aim, the OLED system is made in such a way as to obtain an internal microcavity effect, intended to restrict the spectrum of light emitted, or suitable to transmit the light emitted only in the desired wavelength field.

The microcavity can be either strong or weak, as will be described in more detail hereafter, depending on the type of molecular architecture chosen to make the OLED, in order to minimize losses of radiation emitted due to the effect of the dissipation of electromagnetic energy emitted due to the presence of surface plasmons, or surface polaritons plasmons, in correspondence with the interface between the anode and the organic material that conducts holes.

A thin film 5 of transparent conductive material is interposed between the source 7 and the transparent substrate 2, and advantageously consists of indium-tin oxide, zinc oxide and similar transparent and conductive oxides or gold, silver or alloys thereof. In the case of thin gold or silver films being used, on the surface an adherence promoter layer will first have to be deposited, for example through high vacuum evaporation, consisting of 5 nm of chrome or germanium or carbon in the form of graphite [see P. Melpignano et al., Organic Electronics, 11 (2010), 1111-1119].

The microfluid system 8 preferably consists of a transparent plastic element, obtained by injection molding of plastics such as PMMA (polymethyl methacrylate) or PC (polycarbonate). The system may consist of a series of channels disposed comb-like and separated from each other, or of a single coil-shaped channel, or again of a single fluid expansion chamber 10. In this case the chamber will be rectangular or square with the presence of an inlet channel and an outlet channel for the fluid.

The microfluid system 8 is attached to the substrate 2 where there is the OLED source by means of a mechanical attachment and the hydraulic seal is guaranteed by an elastomeric joint like an O-ring.

The microfluid system 8 can comprise microfluid channels, not shown, having sections able to guarantee a laminar, not turbulent flow of the liquid injected, for example the sample.

On the second surface 4, before the microfluid circuit 8 is attached, a polymeric layer 6 is laid, to adhere the protein probes 12 to the upper surface 4 of the substrate 2.

One possible method to deposit the polymeric layer 6 can be done with the following sequence:

1) Activation of the surface with $O_2$ plasma (for about 10 minutes),
2) Depositing of the polymer by immersion or laying (for about 30 minutes)
3) Rinsing in de-mineralized water,
4) Drying in a vacuum oven (for about 60 minutes).

Following these operations, the protein probes 12 are then deposited on the upper surface of the substrate 2, in a dot-like manner, for example in the form of spots with a diameter varying between about 50 mm and about 1000 mm, by means of known depositing devices, such as for example microarrayers.

Between the transparent substrate 2 and the polymeric layer 6 there is also, in the preferential embodiment shown, a filtering system 9, consisting of a filter, the function of which is to cut the emission frequencies (expressed in terms of wavelength) of the optical source 7 (OLED) around the emission peak of the fluorophore marker.

Figure 5:
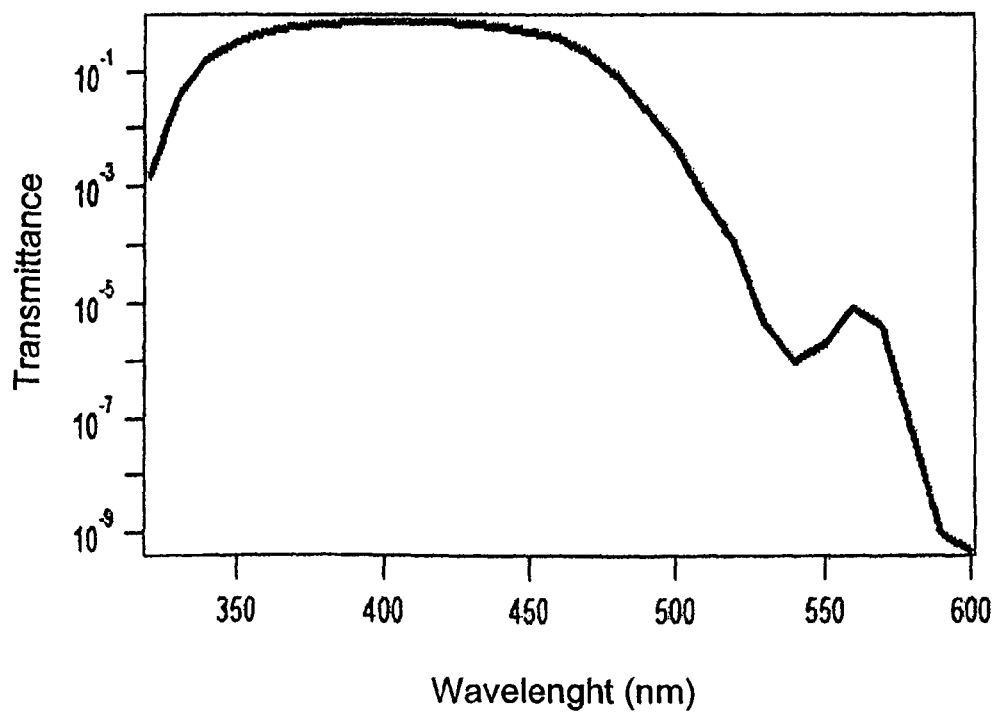
FIG. 5 shows the transmission spectrum of the filtering system associated with the OLED sources in order to excite the marker (fluorophore).

In particular, as can be seen in FIGS. 4 and 5, the filtering system 9 determines a sharp cut (FIG. 5) in the transmittance of the optical source 7 beyond about 520-560 nm, while transmittance is instead at its maximum around 434 nm which represent (FIG. 4) the wavelength corresponding to the absorption peak of the fluorophore used in this example.

With the transmittance characteristics shown in FIG. 5 of the OLED source 7 associated with the filtering system 9, we obtain a maximum fluorescence emission of the fluorophore in correspondence with the wavelength of 540 nm.

In literature it is known that the amplitude of the range ("s") between absorption peak of the fluorophore (in this case 434 nm) and maximum fluorescence emission (540 nm) is called "Stoke's Shift".

According to the invention, the optical source 7 and the filtering system 9 are optimized to maximize the emission of a suitable fluorophore chosen so that the value of "s" is comprised between 25 and 150 nm, which value maximizes the detection sensitivity of the device.

We shall now give a description of the operations actuated by the biochip 1 according to the present invention with relation to the detection of protein molecules inside a sample. It is obvious that this constitutes only one of the possible applications of the biochip 1 according to the present invention.

The biochip 1 according to the present invention provides to conduct the following operations to detect protein molecules (antigens or antibodies) using fluorescent or phosphorescent markers.

Spotting protein probes 12 on the external surface of the OLED.
Fixing the spots on the surface by means of the technique described above.
Fluxing the liquid to be analyzed, for example blood serum or urine.
Rinsing with de-mineralized water.
Fluxing a liquid containing the secondary antibodies linked to a fluorophore, for example AlexaFluor 430.
Rinsing with de-mineralized water.
Ignition of the OLED source and reading the fluorescent spots.
Analysis of the data detected.

The procedure described is similar to a standard ELISA procedure and is known in the field of protein diagnostics (or immune-diagnostics) and therefore will not be described here.

We shall now describe in detail a form of embodiment of the biochip 1 and a detection device associated with the biochip 1.

The biochip 1 comprises a transparent substrate 2, made of glass or plastic or similar material, with a high glass transition temperature $T_g$ with a thickness of about 1 mm.

When a plastic substrate is used, it must have a barrier against oxygen and humidity such as to have a maximum permeability of about $10^{-6}$ gr/m$^2$/day of $H_2O$ and about $10^{-6}$ cc/m$^2$/day of $O_2$.

The thin film 5 preferably has an electric resistivity of less than 10 $\Omega$/sq and a transmittance greater than 85%, in the spectrum range of the visible. The material advantageously consists of indium-tin oxide or zinc oxide or a thin film of gold, silver or alloys thereof.

If there were deposited a thin film (with a thickness comprised between about 10 nm and about 35 nm) of gold or silver on the lower surface 3, to be used as an anode in the case of an OLED with microcavities of the strong type, it will be necessary to deposit on the surface 3 of the substrate 2 a thin film with a thickness of about 5 nm of chrome or germanium or graphite carbon.

The evaporation of the thin gold or silver film in high vacuum is achieved by means of either thermal evaporation or evaporation by electronic cannon with a depositing speed comprised between about 0.5 and about 15 521 /sec and the overall thickness of the thin film can vary within the range comprised between about 10 and about 35 nm.

On the first surface 3 of the substrate 2, in direct contact with the thin film of transparent conductive material 5, there is the optical source 7, in this case consisting of an OLED. By means of high vacuum sublimation an organic multilayer is deposited, consisting of a succession of three or more thin films of small organic molecules constituting the OLED. The thickness of the organic layers deposited and of the material that makes up the anode is calculated to obtain the effect of vertical microcavities of the weak or strong type such as to allow to obtain a half maximum spectrum width of the radiation emitted respectively equal to 40-65 nm and 25-50 nm around the necessary peak wavelength. This reduction in the spectrum width of the light emitted is indispensable to prevent a not-inconsiderable quantity of light from being emitted in the same spectrum region of fluorescence emission of the markers, and thus making the analysis imprecise. The OLED is made using in the emitting layer both electro-phosphorescent materials and also electro-fluorescent materials, inserted in organic matrixes consisting for example of molecules based on diphosphates.

The optical source 7 is advantageously protected fibril the atmospheric agents thanks to a protection system, not shown, that seals the optical source.

In the device described molecular architectures of OLED sources can be used, as described hereafter, to be used in combination with the following commercial fluorophores for marking antibodies: ALEXAFLUOR 430, ALEXAFLUOR 488, ALEXAFLUOR 532, ALEXAFLUOR 546, ALEXAFLUOR 555, ALEXAFLUOR 569 and ALEXAFLUOR 594 (ALEXAFLUOR being the commercial trademark filed by the US Company Molecular Probes), or analogous fluorophores with similar absorption and emission spectrums (within a divergence of ±10 nm from the peak absorption and emission spectrum).

A first molecular architecture represents a weak microcavity OLED device that uses molecules of the electro-fluorescent type, normally used as hole transporters, emitters in the spectrum region of blue and is made as described as follows.
1) Glass substrate with a thickness comprised between about 0.7 mm and about 1 mm.
2) Thin film of Indium Tin Oxide (ITO) with a thickness of about 150 nm±50 nm.
3) Thin film of PEDOT-PSS (Poly(3.4-ethyl-enedioxythiophene)/polystyrene-sulphonate) with a thickness of about 60 nm±10 nm by spin-coating, in a white room class 10 or 100.
4) Thin film of a-NPB (N,N'-bis(1-naphthyl)-5N,N'-diphenyl-1-1'biphenyl-4-4'diamine), deposited by evaporation in high vacuum (comprised between $10^{-6}$ mbar and $10^{-8}$ mbar), with a thickness of about 45 nm±10 nm.
5) Thin film of BCP(2,9-Dimethyl-4,7diphenyl-I,10phenanthroline), also called Bathocupraine, deposited by evaporation in high vacuum (comprised between about $10^{-6}$ mbar and about $10^{-8}$ mbar), with a thickness of about 25 nm±10 nm.
6) Thin film of Lithium Fluoride (LiF), deposited by evaporation in high vacuum (comprised between about $10^{-6}$ mbar and about $10^{-8}$ mbar), with a thickness of about 0.8 nm±0.3 nm.
7) Thin film of aluminum, deposited by evaporation in high vacuum (comprised between about $10^{-6}$ mbar and about $10^{-8}$ mbar), with a thickness of about 100 nm±20 nm.

A second molecular architecture represents a strong microcavity OLED device that uses molecules of the electro-fluorescent type, normally used as hole transporters, as emitters in the spectrum region of blue and is made with the following molecular structure.
1) Glass substrate with a thickness comprised between about 0.7 mm and about 1 mm.
2) Thin film of Germanium (Ge) deposited by evaporation in high vacuum (comprised between about $10^{-6}$ mbar and about $10^{-8}$ mbar), with a thickness of about 5 nm±2 nm.
3) Thin film of silver (Ag) deposited by evaporation in high vacuum (comprised between about $10^{-6}$ mbar and about $10^{-8}$ mbar) at a speed of evaporation comprised between about 0.5 Å/sec and about 15 Å/sec, with a thickness of about 25 nm±5 nm.
4) Thin film of PEDOT-PSS (Poly(3.4-ethyl-enedioxythiophene)/polystyrene-sulphonate) with a thickness of about 40 nm±10 nm by spin-coating, in a white room class 10 or 100.
5) Thin film of a-NPB (N,N'-bis(1-naphthyl)-5N,N'-diphenyl-1-1'biphenyl-4-4'diamine), deposited by evaporation in high vacuum (comprised between $10^{-6}$ mbar and $10^{-8}$ mbar), with a thickness of about 30 nm±10 nm.
6) Thin film of BCP(2,9-Dimethyl-4,7diphenyl-I,10phenanthroline), also called Bathocupraine, deposited by evaporation in high vacuum (comprised between about $10^{-6}$ mbar and about $10^{-8}$ mbar), with a thickness of about 15 nm±10 nm.
7) Thin film of Lithium Fluoride (LiF), deposited by evaporation in high vacuum (comprised between about $10^{-6}$ mbar and about $10^{-8}$ mbar), with a thickness of about 0.8 nm±0.3 nm.
8) Thin film of aluminum, deposited by evaporation in high vacuum (comprised between about $10^{-6}$ mbar and about $10^{-8}$ mbar), with a thickness of about 100 nm±20 nm.

A third molecular architecture represents a strong microcavity OLED' device that uses molecules of the electro-fluorescent type, normally used as electrons transporters, as emitters in the spectrum region of blue and is made with the following molecular structure.
1) Glass substrate with a thickness comprised between about 0.7 mm and about 1 mm.
2) Thin film of Germanium (Ge) deposited by evaporation in high vacuum (comprised between about $10^{-6}$ mbar and about $10^{-8}$ mbar), with a thickness of about 5 nm±2 nm.
3) Thin film of silver (Ag) deposited by evaporation in high vacuum (comprised between about $10^{-6}$ mbar and about $10^{-8}$ mbar) at a speed of evaporation comprised between about 0.5 Å/sec and about 15 Å/sec, with a thickness of about 25 nm±5 nm.
4) Thin film of PEDOT-PSS (Poly(3.4-ethyl-enedioxythiophene)/polystyrene-sulphonate) with a thickness of about 40 nm±10 nm by spin-coating, in a white room class 10 or 100.
5) Thin film of a-NPB (N,N'-bis(1-naphthyl)-5N,N'-diphenyl-1-1'biphenyl-4-4'diamine), deposited by evaporation in high vacuum (comprised between $10^{-6}$ mbar and $10^{-8}$ mbar), with a thickness of about 15 nm±10 nm.
6) Thin film of BAlq3 (Bis-(2-methyl-8-quinolinato)-4-(phenyl-phenolato)aluminum-(III), deposited by evaporation in high vacuum (comprised between about $10^{-6}$ mbar and about $10^{-8}$ mbar), with a thickness of about 45 nm±10 nm.
7) Thin film of Lithium Fluoride (LiF), deposited by evaporation in high vacuum (comprised between about $10^{-6}$ mbar and about $10^{-8}$ mbar), with a thickness of about 0.8 nm±0.3 nm.

8) Thin film of aluminum, deposited by evaporation in high vacuum (comprised between about $10^{-6}$ mbar and about $10^{-8}$ mbar), with a thickness of about 100 nm±20 nm.

A fourth molecular architecture represents a strong microcavity OLED device that uses molecules of the electro-fluorescent type (singlet emission), such as for example those produced by Merck, as emitters in the spectrum region of blue and is made with the following molecular structure.

1) Glass substrate with a thickness comprised between about 0.7 mm and about 1 mm.
2) Thin film of Germanium (Ge) deposited by evaporation in high vacuum (comprised between about $10^{-6}$ mbar and about $10^{-8}$ mbar), with a thickness of about 5 nm±2 nm.
3) Thin film of silver (Ag) deposited by evaporation in high vacuum (comprised between about $10^{-6}$ mbar and about $10^{-8}$ mbar) at a speed of evaporation comprised between about 0.5 Å/sec and about 15 Å/sec, with a thickness of about 25 nm±5 nm.
4) Three thin films with an overall thickness comprised between about 85 nm±10 nm and about 135 nm±10 nm of conjugated organic oligomers, respectively doped conductor of holes, fluorescent emitter in the region of blue with an electro-emission wavelength comprised in the spectrum range of about 410-480 nm, and doped conductor of electrons. The load conductor layers can be made with materials of the dopable organic matrix type, transporters of holes, such as for example the material produced by NOVALED AG, known commercially as NHT-5, and an organic doping material for transporting holes, such as for example the material known commercially as NPD-2, also produced by NOVALED AG, to make the hole transporting layer, and materials of the dopable organic matrix type, transporters of electrons, such as for example the materials produced by NOVALED, known commercially as NET-5 or NET-8, and organic doping materials to improve the transport of electrons, such as for example the materials made by NOVALED known commercially as NDN-1 or NDN-26, to make the electron transporter layer.
5) Thin film of aluminum or aluminum-based alloy, deposited by evaporation in high vacuum (comprised between about $10^{-6}$ mbar and about $10^{-8}$ mbar), with a thickness of 100 nm±20 nm.

The OLED made according to this fourth architecture has a luminance equal to or greater than 1000 cd/m$^2$ if fed with continuous tension in a range comprised between about 2.5 V and about 10 V. The emission spectrum of the OLED has a peak wavelength comprised in the range between about 410 nm and about 480 nm with a maximum width at middle height (FWHM—Full Width Half maximum) comprised between about 25 nm and about 60 nm.

A fifth molecular architecture represents a weak microcavity OLED device that uses molecules of the electro-fluorescent type, normally used as electron transporters, emitters in the spectrum region of blue and is made with the following molecular architecture which provides:

1) Glass substrate with a thickness comprised between about 0.7 mm and about 1 mm.
2) Thin film of Indium Tin Oxide (ITO) with a thickness of about 150 nm±50 nm.
3) Thin film of PEDOT-PSS (Poly(3.4-ethyl-enedioxythiophene)/polystyrene-sulphonate) with a thickness of about 60 nm±10 nm deposited by spin-coating, in a white room class 10 or 100.
4) Thin film of a-NPB (N,N'-bis(1-naphthyl)-5N,N'-diphenyl-1-1'biphenyl-4-4'diamine), deposited by evaporation in high vacuum (comprised between $10^{-6}$ mbar and $10^{-8}$ mbar), with a thickness of about 25 nm±10 nm.
5) Thin film of BAlq3 (Bis-(2-methyl-8-quinolinato)-4-(phenyl-phenolato)aluminum-(III), deposited by evaporation in high vacuum (comprised between about $10^{-6}$ mbar and about $10^{-8}$ mbar), with a thickness of about 55 nm±10 nm.
6) Thin film of Lithium Fluoride (LiF), deposited by evaporation in high vacuum (comprised between about $10^{-6}$ mbar and about $10^{-8}$ mbar), with a thickness of about 0.8 nm±0.3 nm.
7) Thin film of aluminum, deposited by evaporation in high vacuum (comprised between about $10^{-6}$ mbar and about $10^{-8}$ mbar), with a thickness of about 100 nm±20 nm.

To improve detection sensitivity, the use of all the OLED sources described above in order to excite a fluorophore such as ALEXAFLUOR 430 or in any case a fluorophore with excitation and emission spectrums as shown in FIG. 4, an interferential optical filter 9 is provided, or another type, for optical wavelengths of the low-pass type with a cut-off wavelength of 500 nm. In particular, the filter 9 will have a transmittance higher than 0.6 for wavelengths up to 430 nm, and will then decrease to a transmittance of lower than $2.0*10^{-6}$ for a wavelength equal to 540 nm corresponding to the emission peak of the fluorophore used to mark the biological probe. An example of the transmittance curve of the filter is shown in FIG. 5.

On the second surface 4 of the substrate 2, that is, the face the radiation exits from, the polymeric layer 6 is deposited, as previously described, to ensure that the protein probes 12 adhere directly on the external surface of the OLED source, when the OLED device is made directly on a glass with characteristics of transmittance as in FIG. 5, or on a separate slide with a maximum thickness of about 500 nm or a thin plastic layer (with high optical transmittance in the range of the visible, T>0.8).

If the OLED sources are made on a conventional glass substrate it is necessary to provide the insertion of the optical filter 9 as above between the radiation exit surface of the OLED and the slide or plastic substrate on which the biological probes are deposited. The protein probes 12 are then deposited on the external surface of the OLED source, or on a separate slide, by means of a micro-arrayer, such as for example the sciFLEXARRAYER instrument produced by Scienon AG, which comprises a dispenser regulated by a no-contact piezoelectric system, in order to deposit small quantities of proteins. In particular, spots of protein probes 12 can be deposited in dot-like manner with a volume comprised between about 10 nl and about 1 ml. The matrixes of probes 12 can vary from a minimum of 2×2 spots up to a maximum of 15×15 spots on the illuminated surface of the OLED with sizes comprised between 1×1 cm$^2$ and 1.5×1.5 cm$^2$.

Directly on the substrate 2 of the OLED source, or on a separate slide on which the layer 6 of adhesion polymer and the probes 12 have been deposited, the plastic microfluid circuit 8 is mechanically attached.

The microfluid channels are made with a comb shape or with a coil-like path or with a single fluid expansion chamber 10 of sizes such as to entirely contain the matrix of probes 12.

The width of the micro-channels can vary from a minimum of about 10 μm to a maximum of about 1 mm and their height from a minimum of about 1-2 μm to a maximum of about 500 μm. In the case of a single expansion chamber 10, the lateral sizes of the rectangular or square chamber can vary from a minimum of about 1×1 cm$^2$ to a maximum of about 2×2 cm$^2$ with a height varying between a minimum of about 10 μm to a maximum of about 1.5 mm. The fluids to be analyzed and the fluids used for washing enter and exit by means of two channels, a first to inject the fluid and a second for it to exit. The second channel is connected to a suction micro-pump to allow the liquids to be fluxed in laminar flow mode, without inclusions of air or turbulence.

The hydraulic seal of the microfluid circuit is guaranteed by a sealing joint such as an O-ring, and the mechanical seal is obtained by means of attachment elements or clips made in a single piece with the microfluid circuit. The microfluid circuit is then stably coupled either with the substrate of the OLED source, or with the slide as above.

If the probes 12 are obtained on the separate slide, and the microfluid circuit is attached directly on it, the slide and the OLED source are put in direct contact and held together by means of a plastic frame that constitutes the support of the biochip. Empty areas are provided on the frame, for access to the feed contacts of the OLED source, and a possible slit to allow to insert the optical filter between the OLED and the substrate on which the probes are deposited, when the OLED is made on simple glass.

The final sizes of the biochip 1 for analyses vary between about 3×6 cm$^2$ and about 4×9 cm$^2$. The sizes of the illuminated area vary between about 1×1 cm$^2$ and about 1.5×1.5 cm$^2$.

The detection device 20 consists of components as described hereafter.

A CCD or CMOS matrix 23, stably fixed on the detection device 20, allows to detect the signal emitted by the markers. The CCD matrix 23 preferably has a square or rectangular shape with a side varying between about 1 cm and about 4 cm and is made with pixels of a shape varying between about 10 μm and 100 μm. The distance between the CCD matrix 23 and the biochip 1 can vary between about 1 mm and about 5 mm. In a second form of embodiment the distance between the CCD matrix 23 and the biochip 1 can be taken to about 10 cm and a suitable optical focusing system can be inserted between the biochip 1 and the CCD matrix 23, for example a lens, to improve the detection of the fluorescent signal.

In a preferred solution, the system comprises a second interferential filter, in addition to the filter 9, with a pass-band in the range of about 20-40 nm centered on the peak emission wavelength of the markers present in the biochip 1, made in direct contact on the CCD matrix 23 in order to detect the radiation emitted by the sample in turn excited by the optical source 7 below. The interferential filter can be made on a substrate in a separate or freestanding manner, and can be put in front of the active area of the CCD matrix 23 or can be made directly on the surface of the CCD matrix 23. In this latter case the operation can be done by the vacuum depositing of alternate layers of transparent inorganic materials with a high (above 1.8) and low (below 1.4) refraction index.

A suitable miniaturized electronics is integrated inside the device, with the function of feeding the OLED source and of detecting the optical signal and subsequently processing the data detected so as to supply results of the analysis intelligible to a medic. The device is obviously endowed with software to associate the illuminated spots with particular antibodies present in the matrix. Inside the software calibration curves are also implemented in order to associate the intensity of the fluorescence to the quantity of analyte present in the sample.

A display to set the parameters of the analysis and to display the results obtained is associated with the detection device.

The detection device is also endowed with a communication system of the wireless type, for example Bluetooth® or suchlike, to download the data acquired directly onto a PC or portable processor.

The detection device is provided with tanks to contain liquids to wash the biochip 1 and the mixtures with the antibodies marked with the fluorophore. Suction micro-pumps are also provided, to actuate the cycling of the liquids concerned.

The detection device is also provided with a pilotable system to feed the OLED source. The final sizes of the portable detection device can vary between 25×15×10 cm$^3$ and 30×20×20 cm$^3$. The device is fed by means of an integrated battery.

We shall now supply indications concerning the procedures to be used to make the biochip 1 according to the present invention.

The Films of Transparent Conductive Material

A film of indium-tin oxide (ITO) or zinc oxide can be deposited using a standard high vacuum ($10^{-5}$-$10^{-6}$ mbar) sputtering process on a surface of the substrate. The roughness of the covering is preferably <1 nm and has no irregularities or spikes of a height of more than 15 nm.

The Optical Source

The thin organic films that make up the optical source 7 are deposited by high vacuum sublimation with pressures comprised between about $10^{-6}$ mbar and about $10^{-8}$ mbar and with depositing speeds varying between about 0.1 Angstrom/sec and about 15 Angstrom/sec, depending on the type of organic material to be sublimated. The thickness of the layers can vary between about 5 nm and about 150 nm, depending on the type of layer deposited.

The deposit thickness is controlled during the growth phase of the film by means of a suitably calibrated quartz microscales. To calibrate the scales the thickness of the film deposited is controlled by means of profilometric techniques. This control allows to set the instrumental or tooling factor of the scales.

The organic films are deposited in succession using different Knudsen cells for each type of material. The emitter layer of the OLED used as source can consist of a matrix, for example CBP (4,4'-bis-(N-carbazolyl)biphenyl or TCTA 4,4', 4"-Tris(carbazol-9-il)triphenylamine, doped with a suitable organic colorant. The colorant can be either the fluorescent type, such as for example, DCM2 (4-(Dicyanomethylene)-2-metil-6-(julolidin-4-il-vinil)-4H-pirano), or the phosphorescent type, such as for example Ir(ppy)3((Tris[2-(2-piridinil) phenyl-C,N]-iridium) or F(Ir)pic(iridium(III)bis(4,6-(difluorophenyl)-piridinato-N,C2')picolinato)) and the percentages of emitter colorant can vary between 4 and 15%.

The doped organic layers are deposited by co-evaporation, controlling the evaporation speeds or rates of the co-evaporated materials so as to obtain the desired percentages of doping material.

In order to achieve emitter OLEDs in the spectrum region of blue, it is preferable to use emitter materials of the fluorescent type (singlet emission) in the form of single, non-doped layers such as for example BAlq3 (Bis-(2-methyl-8-quinolinato)-4-(phenyl-phenolato)aluminum-(III). This choice is due to the greater stability of such materials when the OLED sources are being used.

The cathode may be deposited both in a separate vacuum chamber, connected to the chamber where the organic materials are deposited by a vacuum loop, so as to prevent the passage of air into the sample to be made, and also in the depositing chamber itself where the thin organic films are deposited. The cathode can be evaporated at a pressure of $10^{-8}$ mbar or with sublimation evaporation techniques or with depositing by means of electronic cannon.

If the cathode is evaporated in the same evaporation chamber as the organics by means of thermal evaporation, it is better to distance the evaporation crucible as much as possible (at least 70 cm) from the sample-bearer so as to avoid overheating and therefore damage to the organic layers that make up the electro-emitter heterojunction.

The cathode may consist for example of Li/Al, LiF/Al, Al/Ca and is evaporated through a metal template with suitable holes to allow to achieve the geometries of the tracks.

The microcavities inside the OLED system can be obtained in two different ways, as will now be described.

In the first way, the thicknesses of the organic materials that make up the OLED are varied depending on their overall refraction index, which entails the consequent variation in the properties of spectrum transmittance of the radiation emitted, in this specific case at an angle 0° with respect to the normal of the device following the method described in B. Y. Jung and C. K. Hwangbo "Determination of an Optimized Alq3 layer thickness in Organic Light emitting Diodes by using microcavity effects"—Journal of the Korean Physical Society, Vol. 48, N. 6 Jun. 2006 and references cited and in Yokoyama, Science, Vol. 256 (1992) p. 66. If the overall thickness of the organic multilayer necessary to make the device were to be more than 150 nm, then doped organic materials will have to be used to make the load transporter layers.

In general, to obtain the microcavities two situations can be considered.

In a first situation, called "weak microcavity", electrodes are used, of which one has a reflectance close to 1 and the second has a smaller reflectance, usually less than 0.5.

In the second situation, called "strong microcavity", both the electrodes have high reflectance and the second electrode can have a reflectance greater than 0.8. In this case, the interference effects of the radiation emitted inside the cavity consisting of the two electrodes are much more marked, with a great narrowing of the spectrum of the radiation transmitted through the second electrode. The efficiency of the optical microcavity is therefore much higher in a narrow range around the peak wavelength of the emission of the emitter organic layer.

In order to obtain the first type of microcavity Indium Tin Oxide (ITO) is generally used as the material for the anode, whereas for the second type of microcavity thin layers are used, with a thickness varying between about 10 nm and about 40 nm of noble metals such as gold or silver. For both configurations the structure and thickness of the organic layers must be optimized, not only to obtain the constructive interference peak around the wavelength concerned, but also to reduce the loss effects due to the presence of surface plasmons at the interface between the organic material that transports holes and the anode. (See R. R. Chance et al. "Molecular Fluorescence and Energy Transfer Near Interfaces", Advances in Chemical Physics, Vol. 37, John Wiley and Sons, p. 16, 1978 and W. L. Barnes "Fluorescence near interfaces: the role of photonics mode density", Journal of Modern Optics, Vol. 45, n. 4, p. 667, 1998).

A second way provides to deposit two or four inorganic layers with a refraction index alternately low (1.4) and high (1.8) on the substrate of the OLED so as to form a cavity resonant at the peak emission wavelength of the organic device. The inorganic layers can be deposited by means of vacuum sputtering and must be deposited between the substrate 2 and the anode of ITO 5. (See J. Lim et al. "Enhanced out-coupling factor of microcavity organic light emitting devices with irregular microlens array"—Optics Express 6564, Vol. 14, N. 14, 2006).

The biochip 1 can be fed both by means of a continuous tension electric source, preferably in a tension range comprised between about 2.5 and about 18V, and also by means of a pulsed tension electric source.

By means of the pulsed feed it is possible to increase the emission of photons from the OLED only during the acquisition time of the CCD sensor. In this way we obtain an increase in the signal noise ratio of the image acquired, generating short flashes of light exactly in correspondence with the integration windows of the CCD sensor.

The temporal structure of the feed impulses is synchronized with the display/integration time of the CCD sensor used to acquire the image produced by the biochip.

The pulsed feed of the biochip provides two functioning modes, both periodic with a period $t_p$ and repetition frequency $f_p$ ($f_p=1/t_p$) varying from about 0.1 Hz to about 1 KHz.

A first functioning mode, "single impulse", has a single impulse for every period $t_p$. The duration of each impulse can vary between about 0.05% and about 50% of the period $t_p$.

A second functioning mode, "train of impulses", provides a sequence of close-up impulses that is repeated with every period $t_p$. The period of time between the close-up impulses is defined as micro-period $t_{MP}$. The micro-period $t_{MP}$ can vary from about 10 microseconds ($10^{-5}$ seconds) to about 1 millisecond ($10^{-3}$ seconds). In this second functioning mode, the duration of each individual impulse can vary from about 1% to about 50% of the period $t_{MP}$. An amplitude modulation can be applied to the train of impulses such that the envelope of the train of impulses has an amplitude varying from about 1% (start of the train of impulses) to about 100% (end of the train of impulses) with a linear growth profile along the train of impulses.

In the reading device of the biochip 1, or reader, the image acquisition sensor is housed, in high-sensitivity CCD (Charge Coupled Device) technology, and also the electronic circuit to feed the OLED and to generate the tension impulses described above.

The circuit to generate the feed impulses and the start-of-acquisition signal are synchronized.

The duration of the acquisition time window of the CCD acquisition sensor varies so as to be added to the duration of the individual light impulse, in the first functioning mode, or the single train of impulses, in the second functioning mode.

Protection System for the Optical Source

In order to seal the optical source 7, a slide is glued by means of a suitable UV reticulable resin on the side of the cathode. The resin must not touch the metal tracks of the cathode and therefore there must be a suitable design of the tracks and the ITO below. Between the slide and the OLED device there must be interposed a getter element to catch possible atmospheric pollutants (oxygen and humidity) that could infiltrate through the resin.

A second option for sealing the OLED device is to deposit a series of layers, alternatively organic and inorganic, some tens of nm thick, directly on the cathode. The layers can be deposited by means of low-power sputtering (to prevent damage to the organic multilayer) in a vacuum chamber.

Alternatively, it is possible to deposit organic and inorganic films with a siloxane base by using cold plasma in conditions of ambient pressure.

The Microfluid System

The microfluid circuit is made using injection molding technology in one of the following transparent plastic materials (transmittance in the visible >0.9): PMMA or PC.

The microfluid channels, or the sole expansion chamber 10, as described previously, are obtained by using nickel molds, made by galvanic growth in an electrolyte bath. The molds are subsequently used for the serial production of the plastic circuits to be used in the biochip.

The molding method must guarantee the sizes of the channels or of the sole expansion chamber 10, described previously in this document, according to maximum tolerances of 10 μm. The fluids to be analyzed and the fluids used for washing enter and exit by means of two channels, one to inject the fluid and the second for it to exit. The second channel is connected to a suction micro-pump to allow the liquids to be fluxed in laminar flow mode, without inclusions of air or turbulence. At inlet to and at exit from the microfluid circuit there may be valves present, for hydraulic regulation or the distribution of the streams of liquid injected.

The hydraulic seal of the microfluid circuit is guaranteed by a sealing joint such as an O-ring, and the mechanical seal is obtained by attachment elements or clips made in a single piece. The microfluid circuit is then stably coupled either on the substrate of the OLED source, or on the slide as above.

Adhesion Layer of the Biological Probes on the Substrate of the OLED Source

To attach the molecules on the external surface of the OLED or on a separate slide, a known polymer is used, such as for example as described in the patent EP 1567569 in the name of the Italian National Research Council (ICRM-CNR). The polymer allows to obtain a uniform covering with a better effectiveness against the non-specific adsorption of molecules. It is also possible to obtain a high surface concentration of reactive groups which allow to immobilize more efficiently the molecules that make up the probes 12.

A first co-polymer used is obtained by means of co-polymerization of dimethyl acrylammide, responsible for self-adsorption on glass, with acryloyloxysuccinimide, responsible for the covalent bonds with the protein molecules, and with (trimethoxysilyl)propyl methacrylate to reinforce the bonding force of the copolymer to the glass.

A second type of polymer consists of a copolymer with blocks consisting of monomers with different functions.

Electric Contacts to Feed the OLED Source

The electric contacts for the OLED source are positioned along the perimeter of the glass substrate so as to allow easy access to the feed terminals. The contacts may be made in a first solution with Indium Tin Oxide (ITO), in a second solution with ITO covered with a thin film of gold or aluminum, to improve the contact resistance, or in a third solution directly with a gold or aluminum film. For the first solution lithographic incision techniques are used, by means of UV exposure and subsequent chemical development, on the glass substrate covered with ITO by using templates that define the geometry. In the second solution, after the operations performed in the first solution, there follows a vacuum evaporation through metal templates, holed in a predetermined manner, to define the geometries of the electrodes. In the third solution only said evaporation is performed.

It is clear that modifications and/or additions of parts may be made to the device 1 to detect analytes in a biological sample as described heretofore, without departing from the field and scope of the present invention.

The invention claimed is:

1. A device to detect at least an analyte, comprising:
a transparent substrate having a first surface, lower during use, with which a light source comprising an OLED source is associated, and a second surface, higher during use, to receive a plurality of biological protein probes; and
a layer of polymer to activate a covalent link with the proteins of the protein probes interposed between said second surface and said biological protein probes, wherein:
at least a marker (fluorophore) is associated with said analyte, having determinate characteristics of fluorescence and/or phosphorescence correlated to the emission wavelength of the light source, wherein
said light source is suitable, or is associated with suitable filtering means, to emit a light radiation in a range of wavelengths equal to 400-550 nm, inside of which is a range of an absorption peak of said marker (fluorophore), and
a value of a distance ("s") between the wavelength corresponding to the absorption peak of the marker (fluorophore) and the wavelength corresponding to the fluorescence (or phosphorescence) emission peak is between 25 and 150 nm,
wherein the OLED source comprises:
a glass substrate with a thickness of between about 0.7 mm and about 1 mm;
a thin film of Germanium (Ge) with a thickness of about 5 nm±2 nm;
a thin film of silver (Ag) with a thickness of about 25 nm±5 nm;
a thin film of PEDOT-PSS (Poly(3,4-ethyl-nedioxythiophene)/polystyrene-sulfonate) with a thickness of about 40 nm±10 nm;
a thin film of a-NPB (N,N'-bis(1-naphthyl)-N,N'-diphenyl-1-1'biphenyl-4-4' diamine), with a thickness of about 30 nm±10 nm;
a thin film of BCP (2,9-Dimethyl-4,7diphenyl-I,10phenanthroline), or Bathocupraine, with a thickness of about 15 nm±10 nm;
a thin film of lithium fluoride (LiF), with a thickness of about 0.8 nm±0.3 nm; and
a thin film of aluminum with a thickness of about 100 nm±20 nm.

2. The device of claim 1, further comprising:
a microfluid system including a transparent plastic material and to contain the protein probes,
wherein said microfluid system includes the sample to be analyzed and said markers (fluorophore) to detect the analyte in direct contact with the upper surface of the substrate.

3. The device of claim 1, wherein the OLED source is configured to obtain an internal microcavity effect on the surface of the transparent substrate, and is for the spectral narrowing of the light emitted so as to transmit the light in a desired wavelength range, correlated to the type of marker used.

4. The device of claim 1, further comprising:
an optical filter for the OLED source for optical wavelengths of a low-pass type with a cut-off wavelength of 500 nm.

5. The device of claim 4, wherein the optical filter has a transmittance of above 0.6 for wavelengths up to 430 nm, and a transmittance of lower than $2.0 *10^{-6}$ for a wavelength equal to 540 nm.

6. The device of claim 1, further comprising:
a continuous tension electric source, in a range of tension between about 2.5 and about 18 V which feeds the OLED source.

7. The device of claim 1, further comprising:
an electric source with pulsed tension synchronous with the acquisition time of an optical detection device which feeds the OLED source.

8. The device of claim 7, wherein said impulse tension is of the "train of impulses" type, in which a sequence of close-up impulses is repeated at every period ($t_p$), and in which the single impulses are repeated at a predetermined micro-period ($t_{mp}$) variable between about 10 microseconds and about 1 millisecond.

9. The device of claim 8, wherein the duration of each single impulse of the "train of impulses" is variable between about 1% and about 50% of the micro-period ($t_{mp}$), and in that said "train of impulses" is modulated in amplitude according to an envelope having an amplitude variable between about 1% in correspondence with the beginning of the train of impulses, and about 100% in correspondence with the end of the train of impulses, with a linear growth profile.

10. The device of claim 1, further comprising:
a detection device, disposed on the opposite side of the light source with respect to the analyte to be analyzed, and including:
a CCD or CMOS matrix to detect the signal emitted by the markers;
an optical focusing system to improve the detection of the fluorescent or phosphorescent signal.

11. The device of claim 10, wherein said detection device comprises a filter, with a pass band in the range of about 20-40 nm centered on a peak emission wavelength of the markers associated with the sample so as to detect the radiation emitted by the sample excited in its turn by the light source below.

12. A device to detect at least an analyte, comprising:
a transparent substrate having a first surface, lower during use, with which a light source comprising an OLED source is associated, and a second surface, higher during use, to receive a plurality of biological protein probes; and
a layer of polymer to activate a covalent link with the proteins of the protein probes interposed between said second surface and said biological protein probes, wherein:
at least a marker (fluorophore) is associated with said analyte, having determinate characteristics of fluorescence and/or phosphorescence correlated to the emission wavelength of the light source, wherein
said light source is suitable, or is associated with suitable filtering means, to emit a light radiation in a range of wavelengths equal to 400-550 nm, inside of which is a range of an absorption peak of said marker (fluorophore), and
a value of a distance ("s") between the wavelength corresponding to the absorption peak of the marker (fluorophore) and the wavelength corresponding to the fluorescence (or phosphorescence) emission peak is between 25 and 150 nm,
wherein the OLED source comprises:
a glass substrate with a thickness of between about 0.7 mm and about 1 mm;
a thin film of Germanium (Ge) with a thickness of about 5 nm 15±2 nm;
a thin film of silver (Ag) with a thickness of about 25 nm±5 nm;
a thin film of PEDOT-PSS (Poly(3,4-ethyl-enediox-ythiophene)/polystyrene-sulfonate) with a thickness of about 40 nm±10nm;
a thin film of a-NPB (N,N'-bis(1-naphthyl)-N,N'-diphenyl-1-1'biphenyl-4-4' diamine), with a thickness of about 15 nm±10 nm;
a thin film of BAlq3 (Bis-(2-methyl-8-quinolinato)-4-phe-nylphenolato) aluminum-(III), with a thickness of about 45 nm±10 nm;
a thin film of lithium fluoride (LiF), with a thickness of about 0.8 nm±0.3 nm; and
a thin film of aluminum, with a thickness of about 100 nm±20 nm.

13. The device of claim 12, further comprising:
a microfluid system including a transparent plastic material and to contain the protein probes,
wherein said microfluid system includes the sample to be analyzed and said markers (fluorophore) to detect the analyte in direct contact with the upper surface of the substrate.

14. The device of claim 12, wherein the OLED source is configured to obtain an internal microcavity effect on the surface of the transparent substrate, and is for the spectral narrowing of the light emitted so as to transmit the light in a desired wavelength range, correlated to the type of marker used.

15. The device of claim 12, further comprising:
an optical filter for the OLED source for optical wavelengths of a low-pass type with a cut-off wavelength of 500 nm.

16. The device of claim 15, wherein the optical filter has a transmittance of above 0.6 for wavelengths up to 430 nm, and a transmittance of lower than $2.0*10^{-6}$ for a wavelength equal to 540 nm.

17. The device of claim 12, further comprising:
a continuous tension electric source, in a range of tension between about 2.5 and about 18 V which feeds the OLED source.

18. The device of claim 12, further comprising:
an electric source with pulsed tension synchronous with the acquisition time of an optical detection device which feeds the OLED source.

19. The device of claim 18, wherein said impulse tension is of the "train of impulses" type, in which a sequence of close-up impulses is repeated at every period ($t_p$), and in which the single impulses are repeated at a predetermined micro-period ($t_{mp}$) variable between about 10 microseconds and about 1 millisecond.

20. The device of claim 19, wherein the duration of each single impulse of the "train of impulses" is variable between about 1% and about 50% of the micro-period ($t_{mp}$), and in that said "train of impulses" is modulated in amplitude according to an envelope having an amplitude variable between about 1% in correspondence with the beginning of the train of impulses, and about 100% in correspondence with the end of the train of impulses, with a linear growth profile.

21. The device of claim 12, further comprising:
a detection device, disposed on the opposite side of the light source with respect to the analyte to be analyzed, and including:
a CCD or CMOS matrix to detect the signal emitted by the markers;
an optical focusing system to improve the detection of the fluorescent or phosphorescent signal.

22. The device of claim 21, wherein said detection device comprises a filter, with a pass band in the range of about 20-40nm centered on a peak emission wavelength of the markers associated with the sample so as to detect the radiation emitted by the sample excited in its turn by the light source below.

23. A device to detect at least an analyte, comprising:
a transparent substrate having a first surface, lower during use, with which a light source comprising an OLED source is associated, and a second surface, higher during use, to receive a plurality of biological protein probes; and
a layer of polymer to activate a covalent link with the proteins of the protein probes interposed between said second surface and said biological protein probes, wherein:

at least a marker (fluorophore) is associated with said analyte, having determinate characteristics of fluorescence and/or phosphorescence correlated to the emission wavelength of the light source, wherein said light source is suitable, or is associated with suitable filtering means, to emit a light radiation in a range of wavelengths equal to 400-550 nm, inside of which is a range of an absorption peak of said marker (fluorophore), and a value of a distance ("s") between the wavelength corresponding to the absorption peak of the marker (fluorophore) and the wavelength corresponding to the fluorescence (or phosphorescence) emission peak is between 25 and 150 nm, wherein the OLED source comprises:

a glass substrate with a thickness comprised between about 0.7 mm and about 1 mm;

a thin film of Germanium (Ge) with a thickness of about 5 nm±2 nm;

a thin film of silver (Ag) with a thickness of about 25 nm±5 nm;

three thin films with an overall thickness comprised between about 85 nm±10 nm and about 135 nm±10 nm of conjugated organic oligomers, wherein the first of said three thin films is a doped conductor of holes, the second of said three thin films is a fluorescent emitter in the region of blue with electroemission with a wavelength comprised in the spectral interval of about 410-480 nm, and the third of said three thin films is a doped conductor of electrons; and a thin film of aluminum or aluminum based alloy, with a thickness of 100 nm±20 nm.

24. The device of claim 23, further comprising:
a microfluid system including a transparent plastic material and to contain the protein probes,
wherein said microfluid system includes the sample to be analyzed and said markers (fluorophore) to detect the analyte in direct contact with the upper surface of the substrate.

25. The device of claim 23, wherein the OLED source is configured to obtain an internal microcavity effect on the surface of the transparent substrate, and is for the spectral narrowing of the light emitted so as to transmit the light in a desired wavelength range, correlated to the type of marker used.

26. The device of claim 23, further comprising:
an optical filter for the OLED source for optical wavelengths of a low-pass type with a cut-off wavelength of 500 nm.

27. The device of claim 26, wherein the optical filter has a transmittance of above 0.6 for wavelengths up to 430 nm, and a transmittance of lower than $2.0 *10^{-6}$ for a wavelength equal to 540 nm.

28. The device of claim 23, further comprising:
a continuous tension electric source, in a range of tension between about 2.5 and about 18 V which feeds the OLED source.

29. The device of claim 23, further comprising:
an electric source with pulsed tension synchronous with the acquisition time of an optical detection device which feeds the OLED source.

30. The device of claim 29, wherein said impulse tension is of the "train of impulses" type, in which a sequence of close-up impulses is repeated at every period ($t_p$), and in which the single impulses are repeated at a predetermined micro-period ($t_{mp}$) variable between about 10 microseconds and about 1 millisecond.

31. The device of claim 30, wherein the duration of each single impulse of the "train of impulses" is variable between about 1% and about 50% of the micro-period ($t_{mp}$), and in that said "train of impulses" is modulated in amplitude according to an envelope having an amplitude variable between about 1% in correspondence with the beginning of the train of impulses, and about 100% in correspondence with the end of the train of impulses, with a linear growth profile.

32. The device of claim 23, further comprising:
a detection device, disposed on the opposite side of the light source with respect to the analyte to be analyzed, and including:
a CCD or CMOS matrix to detect the signal emitted by the markers;
an optical focusing system to improve the detection of the fluorescent or phosphorescent signal.

33. The device of claim 32, wherein said detection device comprises a filter, with a pass band in the range of about 20-40 nm centered on a peak emission wavelength of the markers associated with the sample so as to detect the radiation emitted by the sample excited in its turn by the light source below.

* * * * *